United States Patent [19]

Gallop et al.

[11] Patent Number: 4,659,817
[45] Date of Patent: Apr. 21, 1987

[54] REPORTER COMPOUNDS CONTAINING BORON

[75] Inventors: Paul M. Gallop, Chestnut Hill; Mercedes Paz, Brookline, both of Mass.

[73] Assignee: The Children's Medical Center Corporation, Boston, Mass.

[21] Appl. No.: 638,756

[22] Filed: Aug. 8, 1984

Related U.S. Application Data

[60] Division of Ser. No. 259,705, May 1, 1981, Pat. No. 4,496,722, which is a continuation-in-part of Ser. No. 132,908, Mar. 24, 1980, abandoned.

[51] Int. Cl.$^4$ .......................................... C07D 223/26
[52] U.S. Cl. ................................... 540/541; 540/589; 534/726; 436/544; 436/546; 556/7; 564/8; 564/9; 564/10; 558/285; 558/289; 558/288
[58] Field of Search ...................... 260/462 C, 239 D; 540/589, 541

Primary Examiner—Glennon N. Hollrah
Assistant Examiner—D. B. Springer

[57] ABSTRACT

Compounds and methods featuring, in one aspect, compositions containing an organic boronic acid and one or more reporter groups.

2 Claims, 2 Drawing Figures

REPORTER COMPOUNDS CONTAINING BORON

BACKGROUND OF THE INVENTION

This application is a division of co-pending application Ser. No. 259,705, filed May 1, 1981, now U.S. Pat. No. 4,496,722 which in turn is a continuation-in-part of Gallop et al., "Fluorescent Boronic Acid-Containing Dyes," Ser. No. 132,908, filed Mar. 24, 1980, abandoned.

This invention relates to reporter molecules such as dyes and drugs.

It is often desirable that such molecules be capable of being transferred from one phase to another; e.g., from an aqueous to a non-aqueous phase, or across biological membranes.

It is well-known that certain molecules can be rendered water soluble by the introduction into the molecule of a strongly basic or acidic group such as carboxylic acid or sulfonic acid, which confers water solubility by virtue of being ionized in aqueous solution at certain pH values.

SUMMARY OF THE INVENTION

In one aspect, the invention features a new class of reagents which we have named the Boronate-Dependent Phase Transfer (BorAdept) compounds. The new compounds allow groups which can (1) report on conditions within living cells and tissues or (2) modify metabolic parameters within living tissues to be presented to and taken up by cells under non-toxic conditions.

The new compounds have one of two general formulae:

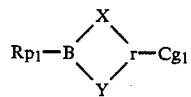  (1)

or

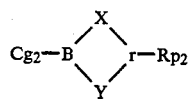  (2)

In both formula (1) and (2), each X and Y, independently, is N, O, or S, and r represents a receptor group which, with X and Y, forms adducts or complexes with boronic acids. $Cg_1$ and $Cg_2$ are carrier groups which each include a solubilizing group which is substantially ionizable in water, and $Rp_1$ and $Rp_2$ are groups which each include a reporter group which is a fluorophore, a chromophore, an organometallic group, a therapeutic agent, an antigen, or an isotopically labelled group.

The new compounds, because of their water-solubility at or near physiological pH, provide reporter groups with greatly enhanced versatility. Further, the ability of formula (1) and (2) compounds to exist in pH-dependent equilibria with their dissociated forms renders them useful for a broad range of applications. Many of these compounds have the additional advantage provided by the boronic acid-derived portion of the molecule which, when dissociated from the remainder of the molecule, can exhibit the selective affinity which boronic acids have for organic compounds having reactive hydroxyl, amino, and thiol groups. The aforesaid equilibria also allow some reporter groups to enter environments where their properties are advantageously altered. For example, some of the fluorescent reporter groups, under certain conditions, can be brought into contact with hydrophobic pockets in cells or organic phases where they exhibit enhanced or quenched fluorescence.

Other aspects of the invention feature applications of the new compounds such as the staining of living cells, proteins, and fabrics, and various assay methods.

Among other aspects, the invention also features new boronic acid containing compounds, which are useful both by themselves, and as starting materials for BorAdept compounds.

Other advantages and features of the invention will be apparent from the following description of the preferred embodiments thereof, and from the claims.

DESCRIPTION OF THE PREFERRED EMBODIMENTS

We turn now to a description of the preferred embodiments of the invention, after first briefly describing the drawings.

DRAWINGS

BORADEPT COMPOUNDS

Figure 1:
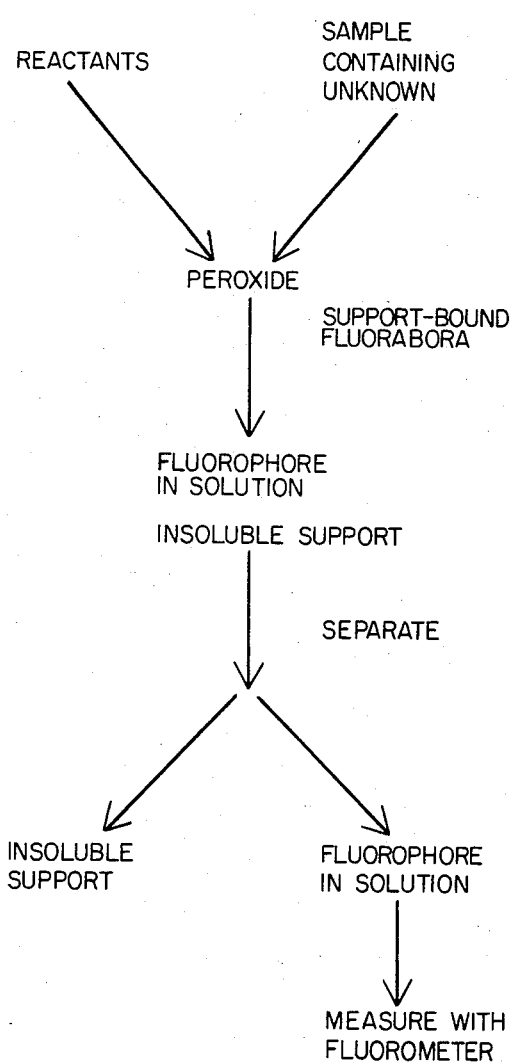
FIG. 1 is a flow chart diagramming an assay method of the invention.

The compounds represented in formula (1) and (2) each is a reaction product between a compound which includes a boronic acid, and a compound which includes a receptor group (r) which, with X and Y, forms adducts or complexes with boronic acids. In both cases, one of the compounds also includes a group ($Rp_1$ and $Rp_2$) which includes a reporter group comprising a fluorophore, a chromophore, an organometallic group, a therapeutic agent, an antigen, or an isotopically-labelled group. The other compound includes a carrier group ($Cg_1$ or $Cg_2$) which includes a strongly basic or acidic solubilizing group which is substantially ionizable in water. $Rp_1$ is bonded to boronic acid in formula (1), while $Rp_2$ is bonded to the receptor in formula (2). $Cg_1$ is bonded to the receptor in formula (1), while $Cg_2$ is bonded to boronic acid in formula (2).

The compounds of formula (1) are generally made by the reaction

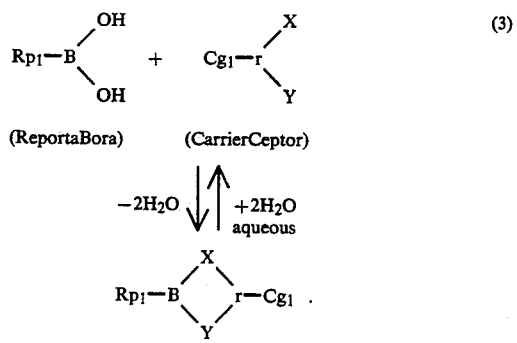

The compounds of formula (2) are generally made by the reaction

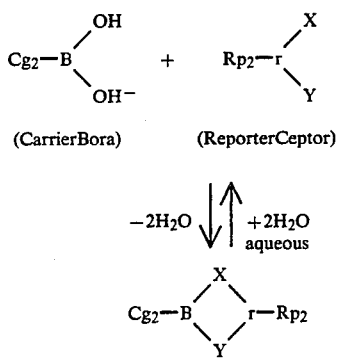

(CarrierBora)     (ReporterCeptor)     (4)

$$Cg_2-B\underset{Y}{\overset{X}{\diamond}}r-Rp_2$$

An important feature of reactions (3) and (4) is that, in aqueous solution, both are reversible; i.e., the BorAdept reagents are in dynamic equilibria with their starting materials. The extent to which, under a given set of circumstances, an equilibrium is pushed in either direction in part determines a compound's usefulness for a given application. The extent to which the equilibrium is pushed toward the formation of the water-soluble formula (1) or (2) compound, at the expense of the starting materials (i.e., pushed to the right) is dependent on several factors, including the pKa and Lewis acid complexing strength of the boronic acid, the complexing potential of

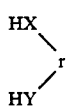

and the local net charge and hydrophobicity of $Rp_1$ or $Rp_2$.

The compounds of formula (1) and (2) can, if desired, contain more than one reporter group, and in such case the properties of the additional group or groups can influence the dynamic equilibrium of the compound.

Turning now to a more detailed description of the compounds of formula (1), the CarrierCeptor portion of the molecule,

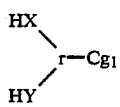

most frequently is of one of three general configurations, so that the formula (1) compound has one of the following general formulae:

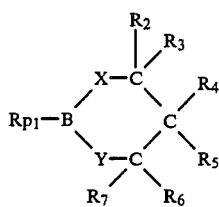

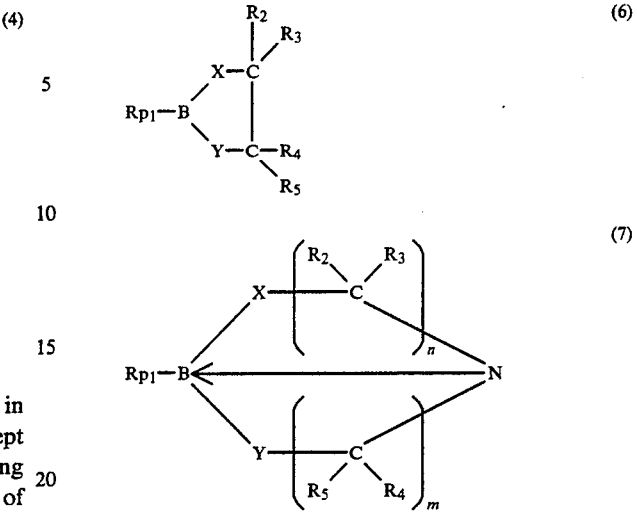

In formulae (5), (6), and (7), each $R_2-R_7$, independently, is hydrogen, aryl, alkyl, heteroalkyl, heteroaryl, aralkyl, or a solubilizing group which is substantially ionized in water, provided that the compound contains at least one such solubilizing group. Each of n and m, independently, is 0, 2, or 3, provided that both cannot be 0. When n or m is 2 or 3, each $R_2-R_5$ can be different in successive repeating units. For example, where n is 2, the $R_2$ attached to the first carbon atom can be hydrogen, while the $R_2$ attached to the second carbon atom is a solubilizing group.

In the structure of formula (7), known as a transanular complex, the arrow from N to B indicates the attraction between the electron-deficient boron atom and the electron-rich nitrogen atom.

In formulae (5), (6), and (7), each of groups $R_2-R_7$ preferably contains between 0 and about 12 carbon atoms. The solubilizing group is preferably a sulfonic acid, a carboxylic acid, quaternary ammonium, a guanidinium group, or a phosphate group.

The first step in making a formula (1) compound is to make the desired ReportaBora. This can be done by reacting a desired organic boronic acid with the desired $Rp_1$. Alternatively, the desired $Rp_1$ precursor can undergo hydroboration with catechol borane, or can participate in a Grignard reaction with a boronate ester to make a ReportaBora. If desired, the reporter group can first be incorporated into a compound having a desired property, e.g., good electron withdrawing power for enhanced activation of the boronate.

Table I shows the structures of some ReportaBora compounds which provide the $Rp_1$-B portion of the compounds of formula (1). Each of these can react with any CarrierCeptor, as defined above, to produce a formula (1) compound. Table I also indicates the utility of the reporter group of each listed ReportaBora. This utility, along with other factors, including choice of CarrierCeptor, allows the choice of starting materials which will react to produce a formula (1) compound possessing the properties required for a given application.

Table II shows the structures and some properties of some preferred CarrierCeptor compounds which provide

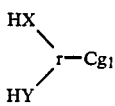

of formula (1) compounds. These CarrierCeptors can be reacted with any ReportaBora, such as those listed in Table I, to make a compound of the general formula (1).

Some of the CarrierCeptors listed in Table II are biologically compatible buffers which have been described in publications from the laboratory of Good, as summarized in Ferguson et al. (1980) Analyt. Biochem. 104, 300; this paper itself also describes suitable buffers. Only the buffers described in the aforementioned literature which contain the

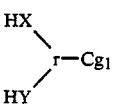

group, as defined herein, are used for making the compounds of formula (1). Table III shows the structures of some preferred formula (1) compounds made with suitable buffers.

Turning now to a more detailed description of the compounds of formula (2), the

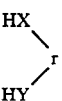

portion of the molecule, as in the case of formula (1) compounds, typically has one of three general configurations, and $Cg_2$ typically includes both a solubilizing group and an organic group linking the solubilizing group to the boron atom. Formula (2) compounds thus typically have one of the following general formulae:

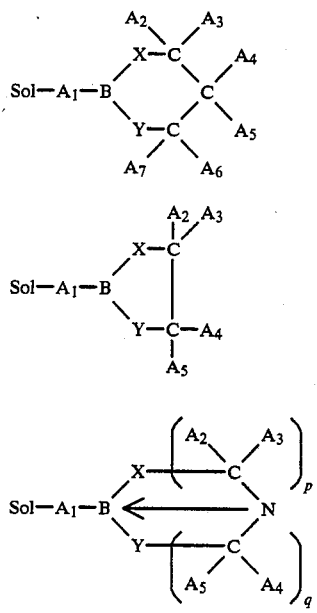

In formulae (8), (9), and (10), Sol is the aforementioned strongly basic or acidic solubilizing group and $A_1$ is alkyl, aryl, heteroaryl, heteroalkyl, or aralkyl;

most preferably $A_1$ contains between 3 and about 12 carbon atoms. Each $A_2$–$A_7$, independently, is hydrogen, aryl, alkyl, heteroalkyl, heteroaryl, aralkyl, or $Rp_2$, the group containing a reporter group, provided that the compound contains at least one $Rp_2$. Each of $A_2$–$A_7$, except $Rp_2$, preferably contains between 0 and about 12 carbon atoms.

Each of p and q, independently, is 0, 2, or 3, provided that both cannot be 0. When p or q is 2 or 3, each $A_2$–$A_4$ can be different in successive repeating units. For example, where p is 2, the $A_2$ attached to the first carbon atom can be hydrogen, while the $A_2$ attached to the second carbon atom can be $Rp_2$.

The first step in making a formula (2) compound is to make the desired ReporterCeptor by reacting the desired $Rp_2$ with the desired

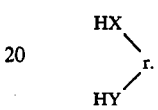

$Rp_2$ can consist entirely of the desired reporter group, or the reporter group can be incorporated into an $Rp_2$ having a desired property; e.g., good reactivity with

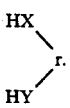

The

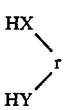

can be any compound which forms adducts or complexes with boronic acids. For example, any of the CarrierCeptors of Table II, with or without their solubilizing groups, are suitable

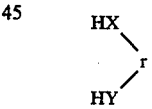

compounds.

A large number of CarrierBoras can be made and reacted with a ReporterCeptor to produce a formula (2). However, there is little advantage (putting aside considerations such as cost) in having a wide variety of CarrierBoras to choose from, and one or a few can be reacted with a wide variety of ReporterCeptors. An example of one such versatile CarrierBora is the compound shown below which, although not commercially available, can be made using conventional methods.

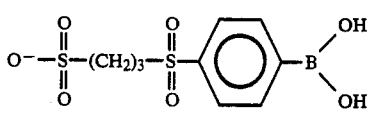

Compound (11) is particularly useful because its boronate group is highly reactive as a result of the strong electron withdrawing action of the sulfonephenyl group

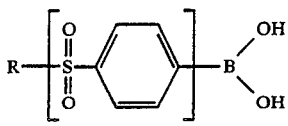

Other examples of CarrierBoras are m-carboxyphenyl boronic acid, p-sulfophenylboronic acid, m-guanidinophenyl boronic acid, and p-trimethylammoniumphenyl boronic acid. The first two are negatively charged, while the latter two are positively charged.

If it is desired to bond a reporter group not only to the boronic acid part of the CarrierBora, but to the linking group as well, it is necessary to provide a reactive site on the $A_1$ portion of the CarrierBora. An example of a CarrierBora having such a site (NH) is

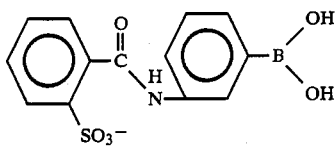
(12)

Compound 12 is made by reacting m-aminophenyl boronic acid, in aqueous ethanol at pH 8.0, with

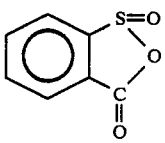
(13)

which is available commercially.

A formula (2) compound is typically made by dissolving the desired ReporterCeptor in an organic, water-miscible solvent, e.g., dimethyl acetamide, acetone, or dimethyl formamide, and then adding an excess of the desired CarrierBora in water or an appropriate aqueous buffer. Some preferred formula (2) compounds are listed in Table IV.

Both formula (1) and formula (2) compounds can, if desired, contain more than one reporter group. A group, $Rp_3$ including a second reporter group can be attached at any suitable reactive site on formula (1) or (2) compounds, but will most often be attached at a site on $Rp_1$ or $Rp_2$ so that the ReportaBora or ReporterCeptor, dissociated from the carrier part of the molecule, bears both reporter groups. Compound 3 of Table III, an example of such a compound, bears two staining reporter groups. Depending on the application, it can also be advantageous to include, in one compound, any of a number of combinations of two of more reporter groups, e.g. a therapeutic agent together with an isotopically labelled group, or a fluorophore together with an antigen.

Staining of Living Cells, Proteins, and Other Materials

The compounds of both formulae (1) and (2) in which the reporter group is a chromophore, an antigen, an organometallic group, an isotopically-labelled group, or a fluorophore are useful for staining living cells, proteins, and other materials such as fabrics and paper products.

The cell-staining formula (1) compounds (hereinafter referred to as "stains") behave differently from those of formula (2), and will be discussed separately.

As shown in equation (3), formula (1) compounds, in aqueous solution at pH values around physiological pH, exist in dynamic equilibria with their starting materials. The equilibrium permits the presentation of the ReportaBora to cells in media compatible with living cells, and uptake by cell membranes without toxicity.

The diagram below illustrates the mechanism of uptake of ReportaBora by cells. The scheme is general, and is not strictly applicable to all formula (1) compounds. For example, a formula (1) compound having a positively-charged solubilizing group such as quaternary ammonium is more likely to enter the cell intact rather than operating as shown below. Also, many ReportaBoras do not exhibit altered reporting properties inside cells.

Equation (3) equilibrium

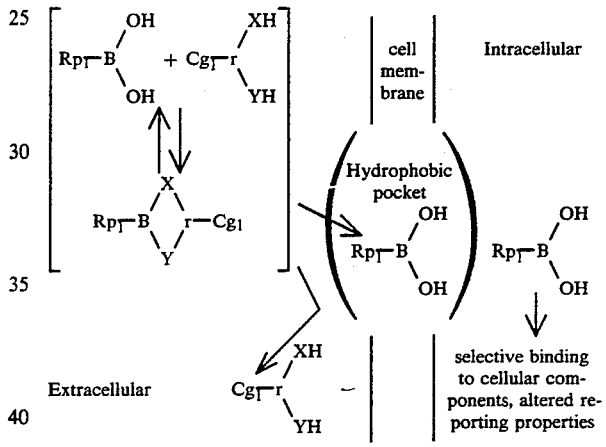

As shown in the diagram, the equation (3) equilibrium permits hydrophobic pockets of the cell membrane to selectively extract ReportaBora, which then enters the cell. Once inside the cell, the ReportaBora, carried by lipophillic components of the cell, is capable of selectively staining cellular components. The boronic acid portion of the molecule binds selectively to certain biological groups within cells which contain appropriately distributed hydroxyl, amino, and thiol groups; binding is particularly favored when such groups are in non-aqueous regions of the cell. Certain complex lipids, mucopolysaccharides, liposaccharides, glycoproteins, and proteins contain such reactive groups. Other compounds, e.g., certain conjugated proteins, also contain such reactive groups in appropriate complexing positions resulting from their sequences, confirmations, and configurations.

The selectivity of formula (1) compounds makes them useful as vital cellular stains in the diagnosis of certain disease states, including certain genetic disorders, particularly those which cause mucopolysaccharidosis, liposaccharidosis, or an increase in either the number or size of cellular lysosomal components. For example, Hurler's Syndrome, Hunter's Syndrome, and β-glucuronidase deficiency can be diagnosed by culturing a patient's cells, staining them with a fluorescent formula (1) stain, e.g., compound 1 of Table III, and then examining them using a fluorescent microscope. The vital staining patterns and the rate of destaining of certain cellular particulates can provide valuable diagnostic information. The compounds are also useful for gaging the viability and motility of human and animal sperm.

The selectivity of formula (1) compounds also makes them useful in comparing staining patterns of various cells in different cell cycle stages. The stains can also be useful for staining catecholamine-rich regions of cells; for example, the compounds stain epinephrine, norepinephrine, dopamine, di-hydroxyphenylalanine, and 3,4-hydroxphenylacetic acid, compounds which are abundant in nervous and adrenal tissue and are thus useful for the diagnosis of a variety of clinical conditions.

Staining of cells can be carried out using any most conventional vital staining techniques, but is preferably carried out according to either of the following two preferred processes.

According to one preferred process, cells to be stained, e.g., fibroblasts, are grown on a coverslip, the culture medium is poured off, the cells are washed with physiological buffer several times, and the coverslip is covered for 5 minutes with a formula (1) compound dissolved in physiological buffer. The coverslip is then washed, turned over onto a slide, and examined using a light or fluorescent microscope, or processed further, e.g., tested for the presence of immune complexes, radioactive label, or heavy metals.

According to another preferred staining method, ReportaBora is added directly to the cell culture medium in which CarrierCeptor is already present as the buffer. After the desired degree of staining is complete, the medium is poured off and the cells are examined.

An additional step may be added to either preferred staining method to obtain additional information, such as the relative dynamic stability of the bonds between the stain and various cellular components. After staining, cells are transferred to fresh culture medium and monitored to determine the relative rates at which the stain leaches out of various cellular components. When the formula (1) compound contains an organometallic electron opaque reporter group, following vital staining, the cells are fixed and prepared for examination with an electron microscope.

Although any formula (1) compounds can be used for vital staining, some are more useful than others for certain applications. One factor affecting choice of dye is the strength of the bond between the ReportaBora and the Carrier Ceptor; very tight complexes, such as those formed with strong CarrierCeptors such as TAPSO, and with certain ReportaBoras containing strong Lewis acid boronic acids, tend to make it more difficult for cell membranes to extract appreciable amounts of the ReportaBora. For this reason, it is sometimes preferable, for vital staining, to use a formula (1) stain made with a weaker complexing CarrierCeptor such as TES or MOPSO (Table II). Because CarrierCeptors which form weak complexes with boronic acids also tend to be less reactive with boronic acids, when it is desired to make a formula (1) compound using a weak CarrierCeptor such as MOPSO, it is often desirable to employ a more reactive ReportaBora; i.e., one in which the boron atom is more electron deficient. Such a reactive ReportaBora is one in which Rp contains a linking group, proximate to the boron atom, which has strong electron withdrawing power. Referring to Table I, FBIII contains the linking group

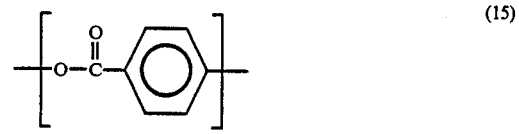

(15)

which, because of its relatively strong electron withdrawing action, renders FBIII able to complex to a considerable degree with weakly complexing CarrierCeptors such as MOPSO. In contrast ReportaBoras, e.g., FluoraBora I, containing groups such as the sulfamido linkage, which do not exert strong electron withdrawing action, complex to a lesser extent with weakly complexing CarrierCeptors, and formula (1) compounds wherein the ReportaBora is Fluoro Bora I are thus preferably made with a strong CarrierCeptor such as TAPSO.

Another factor which can influence the choice of formula (1) fluorescent stain for a particular application is whether the fluorophore is enhanced or quenched (inhibited) in hydrophobic environments such as the hydrophobic protein pockets which the ReportaBora is likely to seek within a cell. Still another consideration is whether the fluorophore exhibits a shift in emission wavelength in such an environment; both enhancement and emission shift can advantageously increase detectability of dyes within cells.

As mentioned above, in the case of formula (1) stains in which the solubilizing group is a positively charged group such as the quanidiuium group (e.g., compound 7 of Table III), rather than just the ReportaBora entering the cell, the entire formula (1) compound may enter. After such a stain has entered a cell, hydrophobic regions of the cell compete with the CarrierCeptor portion for the ReportaBora portion, establishing local intracellular equation (3)-type equilibria. In the case of such a stain in which the reporter group is a fluorophore which is enhanced in hydrophobic environments, varying degrees of enhancement in different parts of a cell are correlated with varying degrees of hydrophobicity in those regions; this data can provide additional information about the properties of the cell.

Formula (2) dyes can also be used for the vital staining of cells. The diagram below illustrates the mechanism of uptake of ReporterCeptor by cells. As with formula (1) compounds, there are exceptions to this general scheme.

Equation (4) equilibrium

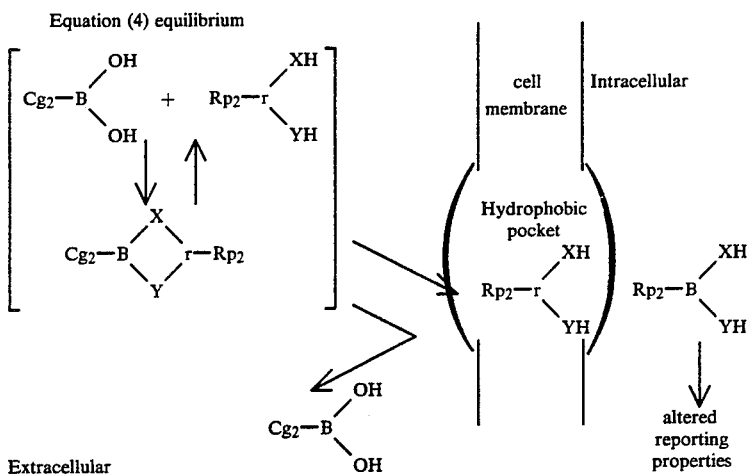

Extracellular

Cells are contacted with an aqueous solution of the stain, which is in dynamic equilibrium with its respective CarrierBora and ReporterCeptor. The cell selectively extracts ReporterCeptor molecules, which enter and stain the cells, and can exhibit altered reporting properties such as fluorescence enhancement or wavelength shift in hydrophobic regions of the cell. Unlike the reporter component of formula (1) stains, those of formula (2) stains are not boronic acids, and do not form such complexes with particular cellular components; their specificity depends instead on the nature of the receptor portion of the molecule.

Formula (2) stains in which the solubilizing group is a positively charged group; e.g. quaternary ammonium, can also be used for vital cell staining. As with formula (1) stains containing such groups, the entire compound may enter the cell and establish local hydrophobicity-dependent equilibria within the cell.

A further refinement to vital cell staining using formula (1) and (2) compounds is to employ a stain having more than one staining reporter group. For example, a formula (1) stain can have the structure

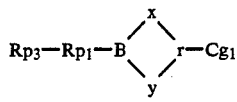

where $Rp_1$ and $Rp_3$ each is a group which includes a fluorophore, chromophore, an antigen, an isotopically-labelled group, or an organometallic compound. Compound 12 of Table I, complexed with TAPSO (Table II) is an example of such a compound, bearing a fluorophore which provides cellular information at the level of the fluorescent microscope, and an electron-opaque organometallic group which provides information on the electron microscope level; the fluorescence pattern of a stained cell indicates to the electron microscopist that that cell took up stain, indicates which portions of the cell were stained at the level of resolution of the light microscope, and, after preparation for electron microscopy, allows a comparison of staining patterns within the same cell at the light and ultrastructural levels.

The formula (1) stains can also be used to permanently stain proteins. The preferred method for carrying out such staining is to react the protein to be stained with the dye under mild conditions; e.g., at room temperature or lower, at pH 4 to 10, in the absence of an organic solvent. Excess ReportaBora can then be removed by carrying out dialysis against the CarrierCeptor used to make the strain. For example, to stain serum albumin, compound 9 (Table III) is first made by dissolving highly water-insoluble ChromaBora II (CBII) (Table I) in a very small volume of dimethyl acetamide and then in an excess of TAPSO at pH 9.0. Serum albumin is then added and the mixture then dialyzed against TAPSO to remove excess CBII. Before the dialysis, CBII enters the hydrophobic pockets of serum albumin, leaving its CarrierCeptor, TAPSO, in the aqueous phase. Dialysis against TAPSO removes excess CBII as the formula (1) complex, but is unable to remove CBII from the hydrophobic pockets of the serum albumin, which is thus permanently stained.

Formula (1) and (2) compounds can also be used to stain or brighten a variety of other materials such as fabrics and paper products. Staining is carried out by simply contacting the material to be stained with an aqueous solution of the desired formula (1) or (2) compound (generally a colored or a fluorescent compound) until the desired degree of staining has been achieved.

Brightening of fabrics is carried out using a fluorescent formula (1) or (2) compound, and can often be performed in a conventional clothes washing machine, in soapy or clean water. Many fabrics can be brightened using the new compounds, including cellulose-containing fabrics such as cotton and linen, and nitrogen-containing fabrics such as wool and silk, and various synthetics. When brightening a cellulose-containing fabric, it is preferable to use formula (1) compounds, because the FluoroBora of the equation (3) equilibrium is attracted to the hydroxyl groups of the fabric.

When brightening a nitrogen-containing compound such as wool, formula (1) dyes are also preferred, and the brightening process may include an additional step. Following the step of contacting the fabric with the fluorescent formula (1) compound, the fabric is contacted with an oxidizing agent such as peroxide, which breaks the carbon-boron bond of the formula (1) compound, releasing $Rp_1$-OH, which is then better locked into the hydrophobic pockets in the fabric. Even greater brightening can be obtained by employing a formula (1) compound in which the fluorescent part of the molecule exhibits enhanced fluorescence in hydrophobic environments.

Peroxide and Enzyme Assays

A colored or fluorescent formula (1) compound can be used to measure, in aqueous solution, an unknown amount of a compound which participates in an enzymatic procedure ("procedure", as used herein, includes one or a series of reactions) in which an enzyme acts on a substrate, or a chemical procedure which results in the production of peroxide.

In the peroxide assay, excesses of all of the reactants participating in the procedure are introduced into a reaction zone, e.g., a test tube, along with the sample containing an unknown amount of the compound to be assayed. The peroxide produced is brought into contact with a known amount of the formula (1) compound. The peroxide, an oxidizing agent, breaks the carbon-boron bond of the ChromoBora or FluoroBora, releasing $Rp_1$-OH, which is then contacted with a substance having a greater affinity for $Rp_1$-OH than for the formula (1) compound. The fluorescence or color intensity of the substance is then measured as a measure of the unknown amount of the compound being assayed.

The selective affinity substance can be a water-immiscible organic solvent which is capable of extracting $Rp_1$-OH away from the formula (1) compound. The solvent forms a fluorescent organic layer separate from the aqueous layer; if desired the two layers can then be separated to facilitate quantification of the fluorescence of the organic layer.

One factor which influences the choice of formula (1) compound when a water-immiscible organic solvent is to be used is the tightness of the complex between the ReportaBora and the CarrierCeptor. Compounds in which the complex is very tight are most preferred because a looser complex may be broken between the boronate and the CarrierCeptor, thus allowing the colored or fluorescent starting material, along with $Rp_1$-OH, to be partially extracted by the solvent. Furthermore, in the case of a looser complex, the tendency of the organic solvent to push the equation (3) equilibrium toward dissociation of the complex by extraction of the ReportaBora may overshadow a comparatively smaller peroxide effect.

Table V shows the extent to which three FluoraBoras, complexed with six CarrierCeptors in aqueous solution, are extracted into ethyl acetate. Of the compounds of Table V, those made with comparatively tightly-complexing TAPSO are most preferred for the peroxide assay because, absent peroxide (i.e., in a blank reaction), a comparatively large proportion of the fluorescence remains in aqueous solution, unextracted by ethyl acetate. Compounds in which the complex is even tighter, so that the blank extraction value is still lower, would be even more desirable.

Another factor influencing the aforesaid choice, when the reporter group of the formula (1) compound is a fluorophore, is the manner in which the organic solvent being used affects the properties of the fluorophore. Some fluorophores are enhanced, i.e., their fluorescence is made more intense, in a given organic solvent, while others exhibit diminished fluorescence (quenching). Some fluorophores may also exhibit altered emission spectra in certain organic solvents. Although any fluorescent formula (1) compound can be used, provided its fluorophore is not totally quenched in the organic solvent, both enhancement and spectrum alteration desirably heighten detectability.

Table VI shows the relative fluorescence of three FluoraBoras combined with TAPSO, compared to the fluorescence of equal concentrations of FluoroBora in the water-immiscible organic solvent ethyl acetate. Because FBPA and FBI are enhanced (two and sevenfold, respectively), formula (1) compounds made with them are suitable for use in the peroxide assay described above. FBIII, on the other hand, is quenched to a large extent in ethyl acetate, and formula (1) compounds made with it are therefore not desirable for use in the assay in which ethyl acetate is employed.

Instead of a water-immiscible organic solvent, the selective affinity substance in the peroxide assay can be a water-miscible protein which has a greater affinity for $Rp_1$ than for the corresponding formula (1) compound being used. Preferred proteins are those, e.g., serum albumin, which possess hydrophobic pockets which can attract $Rp_1$.

When such a protein is used, it is necessary that the formula (1) compound be fluorescent, and that the protein be capable of producing an observable effect, preferably enhancement or, less preferably, quenching, of fluorescence, of $Rp_1$, there being no easily observed water/protein phase separation. Table VII shows the relative enhancement or inhibition with serum albumin, of the three fluorophores of eighteen formula (1) compounds. Table VII shows that, in general, FBI and, to a lesser extent, FBPA, are enhanced in serum albumin, while FBIII exhibits diminished fluorescence.

The extent to which each of the three fluorophores of Table VII is enhanced or inhibited depends, to a significant extent, on the CarrierCeptor with which it is combined. Thus, enhancement, in serum albumin, of FBPA and FBI, and inhibition of FBIII, is much greater if the formula (1) compound has been made with loosely complexing MOPSO than with tightly complexing TAPSO. This is because the loose $Rp_1$-MOPSO complex favors an equilibrium in which more free $Rp_1$ is available to seek the hydrophobic pockets of serum albumin, where enhancement or inhibition of fluorescence occurs. Before performing an assay, therefore, a blank should always be run in which the peroxide-generating reagents are not added, so that enhancement or inhibition in the absence and presence of those reagents can be compared.

The other observable effect which a water-miscible protein such as serum albumin can have on a fluorophore is a shift in the peak emission spectrum; such a shift can, as in the case of a water-immiscible organic solvent, aid detectability. FBPA, for example, normally emits at 460 nm, while its dissociated fluorophore, in the hydrophobic pockets of serum albumin, emits at 427 nm.

Glucose is an example of a compound which can be measured using the above-described method. A sample containing an unknown amount of glucose is placed in a test tube with a known amount of Compound 1 (Table III) and a known amount of serum albumin in aqueous solution at pH between 8 and 9. An excess of glucose oxidase is then added, and the increase in fluorescence compared to that of a no-enzyme, no-substrate blank is measured as a measure of the amount of peroxide produced, which in turn is a measure of the amount of glucose in the sample.

Here, glucose oxidase catalyzes the oxidation of glucose to gluconic acid by oxygen, forming $H_2O_2$. The $H_2O_2$ oxidizes the C-B bond of FBI in the formula (1) complex, forming dansylamido phenol, which enters the serum albumin pockets, where it exhibits enhanced fluorescence.

Using principles similar to those just described, certain formula (1) compounds can also be used to measure an unknown amount of a compound which participates in an enzymatic procedure in which an enzyme acts on a substrate. The method employs fluorescent formula (1) compounds in which $Rp_1$ includes a group, positioned between the boron atom and the fluorophore, capable of acting as a substrate for the enzyme. A desired enzyme substrate can be incorporated into a desired formula (1) compound using conventional techniques.

According to the assay methods, the formula (1) compound being used is introduced into a reaction zone, along with excesses of all of the other participating reactants except the compound to be measured, and a sample containing the compound to be measured. The enzymatic reaction releases modified fluorophore which, after completion of the reaction, is contacted with a water-immiscible organic solvent or a water-miscible protein, as described above for the peroxide assay. The extent of fluorophore extraction or fluorescence enhancement or inhibition is then measured versus a blank, as described above, as a measure of the unknown compound.

If a water-miscible protein is used, the rate of the enzymatic reaction can also be followed by measuring the rate at which fluorescence enhancement increases.

Esterases such as lipases are examples of compounds which can be assayed using this method. In a test tube, in aqueous solution, is placed a known amount of compound 6 (Table III), of the formula

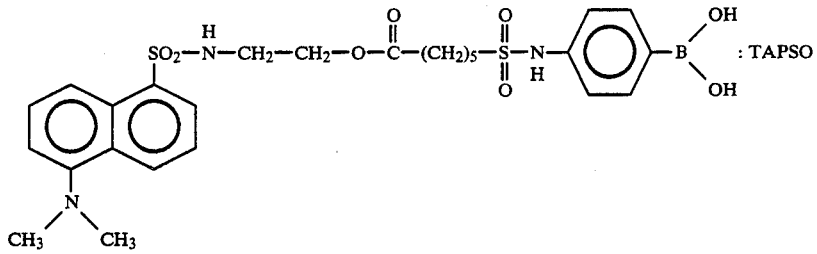

A sample containing an unknown amount of lipase is then added. Lipase present in the sample breaks the ester bond (as indicated by the dotted line), releasing modified $Rp_1$, containing the fluorescent dansyl group, which is then extracted or contacted with a known amount of serum albumin and fluorescence measured, as described above for the peroxide assay.

Antibody Assay

Another new assay employing formula (1) compounds is an antibody assay employing red blood cells. (Red blood cells are commonly used in other antibody assays.) A formula (1) compound is used in which the reporter group of $Rp_1$ is a hapten capable of complexing with the antibody being assayed. Red blood cells are contacted, in aqueous solution, with the formula (1) compound, which is in an equation (3)-type equilibrium with its starting materials. The red blood cell membrane selectively extracts hapten-containing ReportaBora, thus becoming sensitized. The sensitized red blood cells are contacted with a sample containing an unknown amount of antibody, together with complement which is capable of participating in the complexation of the hapten with the antibody. The antibody in the sample complexes with the hapten in the sensitized cell membrane, fixing complement and causing cell lysis and the release of hemoglobin from the cell. The amount of hemoglobin released is a measure of the amount of antibody in the sample.

A modification of the above-described procedure can be performed using red blood cell ghosts or membranes rather than intact cells. According to this modification, the formula (1) compound used contains two reporter groups; a hapten and a fluorophore, both of which become incorporated into the membranes of sensitized red cell ghosts by the BorAdept process. When the ghosts are contacted with antibody and complement, lysis of the ghost stroma occurs, causing the release of soluble fragments containing fluorophore. If desired, the solution can contain a CarrierCeptor to facilitate solubilization of the fluorescent fragments. The fluorescence in solution is then measured as a measure of the antibody titer.

Solubilization of Therapeutic Agents

The BorAdept system of the invention can greatly facilitate the administration of therapeutic agents such as drugs which have heretofor been difficult to administer because of poor water solubility or difficult to test in cell culture systems. A desired therapeutic agent can be incorporated into either a formula (1) or (2) compound. In either case, by virtue of the equation (3) or (4) equilibrium, the agent is not only solubilized, but is in a form which enables the agent to be presented to and taken up by cells to which it is desired to deliver the agent, by the same mechanism by which fluorophore reporter groups are taken up by cells to be stained.

Therapeutic formual (1) compounds are generally made in the same way fluorescent formula (1) compounds are made; i.e., the desired therapeutic agent or a suitable precursor or derivative thereof is first reacted with the desired boronic acid to form a ReportaBora (in this case, a TheraBora), which is then reacted with the desired CarrierCeptor. The boronic acid is preferably chosen to include a group which renders the boronic acid reactive with the therapeutic agent being used.

Compound 4 of Table III is an example of a formula (1) compound containing a derivative of therapeutic agent, the water-insoluble anti-convulsant diphenyl hydantoin. Another example is compound 2 of Table III, containing a derivative of the water-insoluble anti-epileptic drug carbamazepine. This new compound is made according to the reaction scheme illustrated on the following page.

Therapeutic formula (2) compounds are generally made in the same way that fluorescent formula (2) compounds are made, i.e., the desired thereapeutic agent or a suitable precursor or derivative thereof is, if necessary, incorporated into a compound having a desired property to make Rp2, which is then reacted with a compound of the formula

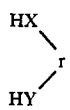

to make the ReporterCeptor, which is then reacted with the desired CarrierBora.

Compound 5 of Table IV is made according to the reaction scheme illustrated on the following page.

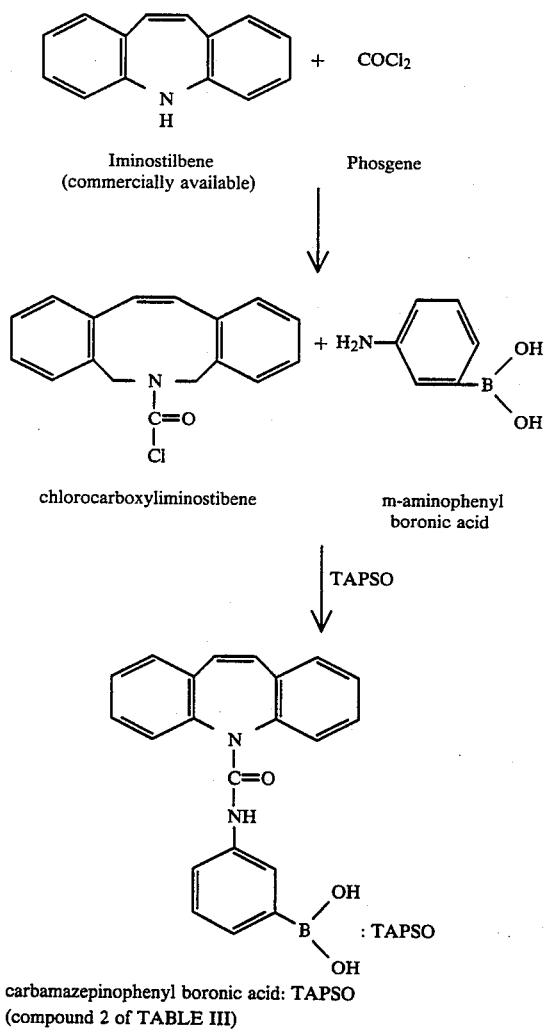

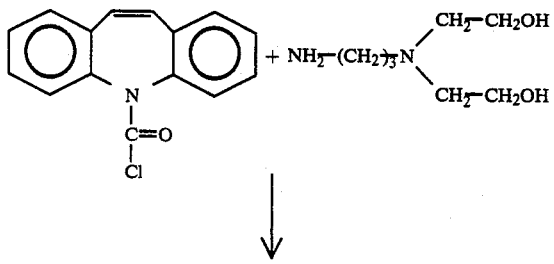

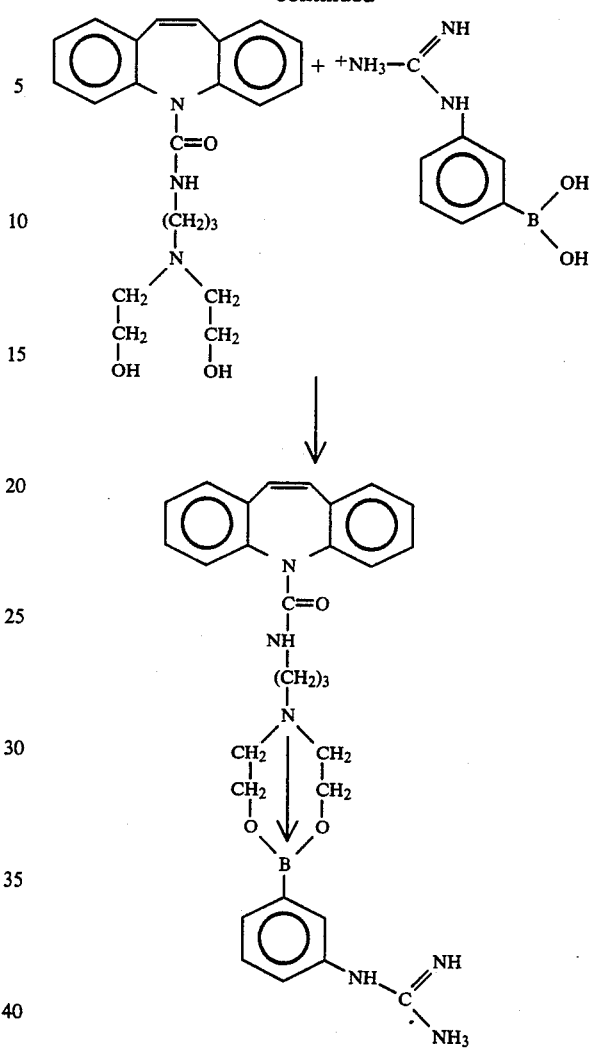

ReportaBoras

Table I lists some preferred ReportaBoras of the invention. These new compounds, as is discussed above, are useful in making formula (1) BorAdept compounds. In addition, we have discovered that they have many applications by themselves, even when not complexed with a CarrierCeptor in a formula (1) compound. Many of these applications, e.g., the peroxide assay, are similar in principle to applications of formula (1) compounds.

The ReportaBoras of the invention are generally made by reacting a desired reporter group-containing compound (Rp4) with a desired organic boronic acid capable of reacting with that Rp4.

Usually the organic boronic acid has the general formula

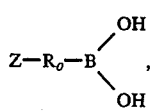

where $R_o$ is aryl, alkyl, heteroalkyl, heteroaryl, or aralkyl, and Z is a group capable of chemically combining with the Rp4 being used. Preferably, $R_o$ contains between 3 and about 25 carbon atoms. A preferred (because of ready availability) boronic acid is m-aminophenyl boronic acid, in which Z is NH and $R_o$ is

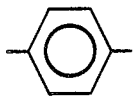

$Rp_4$ usually has the formula

where Re is the reporter group and Y is a group capable of chemically combining with the Z portion of the boronic acid being used.

The ReportaBoras made by reacting the aforesaid boronic acids and $Rp_4$'s thus either have the formula

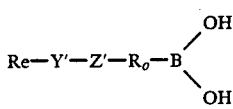

or

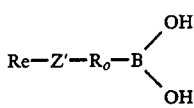

depending on whether Y is entirely lost in the course of the reaction.

In some preferred boronic acids, Z is $NH_2$, OH, SH, or COOH, and in some preferred $Rp_4$'s Y is X,

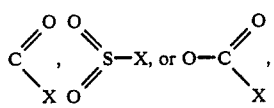

X being any halogen. In ReporterBoras made from these starting materials, the carbon or sulfur atom of Y to which X was bonded bonds to Z, replacing an H. Z' is thus Z minus an H, and Y' is Y minus X. (There is no Y' when Y consists entirely of X).

The boronic acids wherein Z is $NH_2$ can also react with $Rp_4$'s in which Y is N=C=V, where V is O or S. The resulting ReportaBoras have the formula

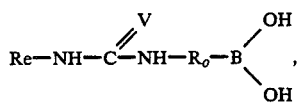

Y' being

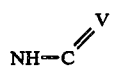

and Z' being NH.

One of the most preferred new ReportaBoras we have synthesized is referred to in Table I as "FBPA". This compound is made using a diaryl pyrazoline sulfonic acid, supplied to us as a gift by Ilford Limited, Basildon-Essex, England. Ilford's fluorescent compound has the formula:

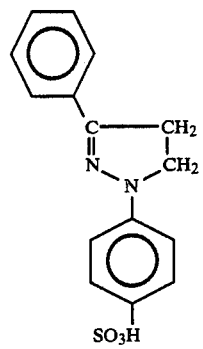

The first step in our synthesis of FBPA is to make the sulfonyl chloride of Ilford's compound by reacting it with $PCl_5$. The new sulfonyl chloride has the formula:

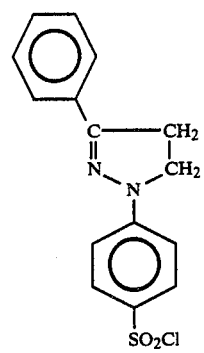

The new compound has a chemically stable crystalline structure with a melting point of 119° C. Besides being useful for making ReportaBoras, it is, also useful as a fluorescent reporter for labelling proteins such as antibodies and other compounds such as amino acids and polyamines. Because of its azure fluorescence, it can be used in conjunction with red and yellow fluorescent dyes in immunofluorescent labelling experiments.

Compound 21 is a diaryl sulfonyl chloride, and is one of a family of fluorescent compounds which we refer to as DARPSYL chlorides. These compounds are the sulfonyl chloride derivatives of compounds of the general formula

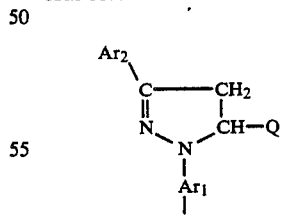

where one of $Ar_1$ or $Ar_2$ is an aromatic group containing a sulfonyl chloride group and Q is hydrogen or an alkyl group. The compounds in which $Ar_1$ contains the sulfonyl chloride group are the "A" compounds, and are derived from the DARPSYL compounds described in British Pat. No. 670,857. The sulfonyl chloride derivatives in which $Ar_2$ contains a sulfonyl chloride group are the "B" compounds, and are also useful fluorescent stains.

The new A-DARPSYL chloride, (compound 21), as well as other DARPSYL-chlorides, can be combined with organic boronic acids to make useful FluoraBoras. To make FBPA (Table I), the A-DARPSYL chloride described above is combined with m-aminophenyl boronic acid in DMF-H$_2$O. The mixture is then acidified, water is added causing FBPA to precipitate out and recrystallization is carried out, from cyclohexane.

Another FluoraBora listed in Table I, FBI, is made by adding an acetone solution of dansyl chloride to an aqueous acetone solution of m-aminophenyl boronic acid hemisulfate containing 2.5 equivalents of sodium bicarbonate, and then acidifying the solution, adding more water causing FBI to precipitate out and recrystallizing from benzene.

FBII, another FluoraBora, is made by adding solid fluorescein isothiocyanate to an aqueous alkaline solution of m-aminophenyl boronic acid.

Many of the ReportaBoras listed in Table I are not fluorescent,, but rather contain reporter groups such as chromophores or derivatives of therapeutic agents. The reporter group can also be an antigen or an isotopically-labelled group, or it can be an organometallic group, as in compounds 8 and 15 of Table III. Compound 12 of Table III also contains an organometallic group, and in addition contains the fluorescent dansyl reporter group. Compound 8 is made according to the reaction diagrammed below.

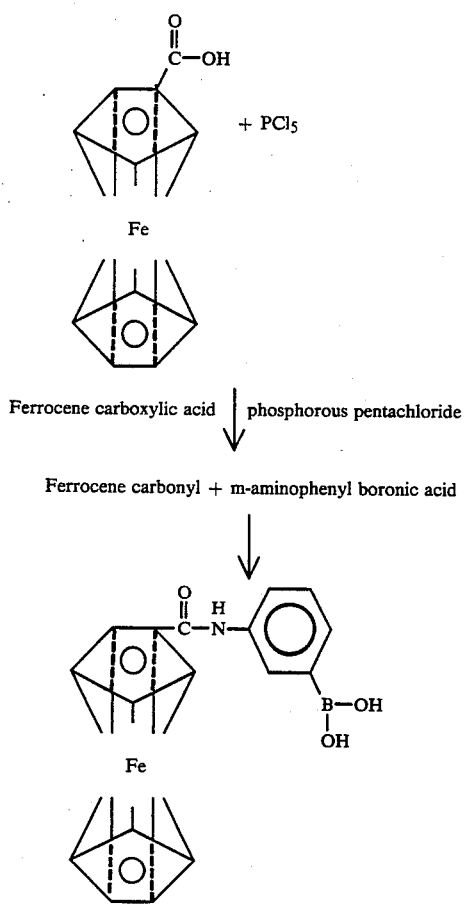

In addition to the mercury and iron-containing complexes of the compounds of Table I, any desired organometallic complex can be used to make a ReporterBora, which in turn can be combined with a CarrierCeptor to make a BorAdept reagent. As is mentioned above, other useful organometallic complexes contain heavy, electron-opaque metals such as osmium, which are useful in staining for electron microscopy.

Cell Staining with ReportaBoras

Many of the ReportaBoras of Table I possess such poor water solubility that they cannot be presented to and taken up by living cells under non-toxic, physiological conditions. Such compounds, as has been discussed, are rendered useful for vital staining only when coupled to a CarrierCeptor.

Some ReportaBoras, e.g., FBI, however, are sufficiently water-soluble, and possess the necessary neutral or positive charge and are sufficiently hydrophobic, to be useful directly as vital stains. Such ReportaBoras are generally used for selective vital staining in the same manner as are BorAdept vital stains, described above.

ReportaBoras and ReporterCeptors can also be used to selectively stain fixed cells, using conventional techniques and solvents. As with vital staining, the selectivity provided by the boronic acid portion of the ReportaBoras can provide valuable diagnostic information.

Certain non-toxic ReportaBoras are useful for vitally staining the surfaces of cells and extracellular areas, and are also useful for staining the eye surfaces of living animals to determine the location of surface irregularities such as scratches and lesions; the negatively charged ReportaBoras are particularly useful for the latter purpose. To stain eye surfaces, the desired ReportaBora, dissolved in a physiological buffer or CarrierCeptor as a formula (1) complex, is applied in any conventional manner, e.g., with an eyedropper.

Support-bound FluoraBoras

FluoraBoras can be bound to certain water-insoluble supports and used in peroxide and other assay methods. The supports which can be used include all organic, water-insoluble polymeric materials having hydroxyl groups which can complex with boronic acids. Examples of suitable supports are polymers containing polyglycerol methacrylate, and hydrophilic fibrous polyethylene containing attached polyvinyl alcohol; the latter support is available from Crown Zellerbach under the name "Fybrel". Support-bound FluoraBoras preferably are made by reacting a solubilized FluoraBora (in acetone, benzene, DMF, or the like) with the powdered form of an appropriate support material and then washing the powder with a solvent to remove excess FluoraBora. Alternatively, if the FluoraBora being used is water-insoluble, it is first complexed with a suitable CarrierCeptor to form a formula (1) BorAdept compound, as described above. If a CarrierCeptor is used, it and the support should be chosen so that the support tends to form stronger complexes with the boronate of the FluoraBora being used, at the pH under which the reaction is carried out, then does the CarrierCeptor at that pH. The equation (3) equilibrium then allows the support to act as a separatory funnel, complexing with dissociated FluoraBora. Usually a weakly complexing buffer such as MOPSO will be used in this situation.

FluoraBoras bonded to Fybrel are particularly preferred embodiments of this aspect of the invention. The structure of FBI so bound is shown below. It can be seen that the boron atom forms a stable 6-membered ring with three carbons and two oxygens of the polyvinyl alcohol.

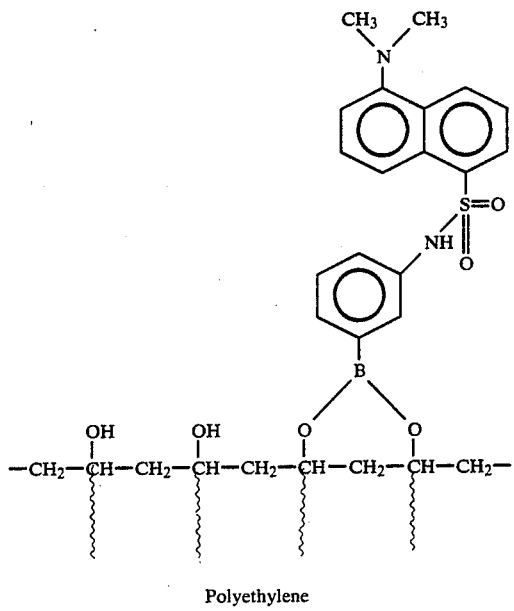

Polyethylene

FBI bound to Fybrel is made as follows. FBI is dissolved in acetone. Fybrel is ground to coarse powder and shaken with the dissolved FBI for 5 minutes. After exhaustive washing with acetone, support-bound FBI is stored in the dark at 5° C. until used, either dry or in an organic solvent.

Peroxide Assay

Flow Chart I (FIG. 1) diagrams a method for assaying, in aqueous solution, a compound which participates in a chemical procedure which results in the production of peroxide. The basic principle is the same as that of the BorAdept peroxide assay, previously described. Excesses of all of the reactants participating in the procedure are introduced into a reaction zone, e.g., a test tube, along with the sample containing an unknown amount of the compound to be assayed. The peroxide produced is brought into contact with a support-bound FluoraBora, described above. The peroxide, an oxidizing agent, breaks the carbon-boron bond of the boronic acid, releasing fluorescent compound into solution, where it can be measured directly using, e.g., a fluorometer, enhanced using a protein such as serum albumin, or extracted using a water-immiscible organic solvent such as ethyl acetate.

The rate of release of fluorescent compound can be increased by maintaining the pH of the reaction zone in the range of about 8 to 9. The assay can be further modified by separating fluorescent compound in solution from the insoluble support following the oxidation of the carbon-boron bonds by the peroxide. This separating can be carried out by filtering, by removing the insoluble support using centrifugation, or by extracting the dissolved fluorescent compound in an organic, water-immiscible solvent.

Glucose is an example of a compound which can be assayed using the above-described method. To a sample, in aqueous solution, containing an unknown amount of glucose are added aqueous buffer of pH 8 to 9, glucose oxidase, and an excess of FBI bound to Fybrel. After the release of fluorescent compound into solution has been completed, the Fybrel is filtered out and fluorophore is measured, using a fluorometer, as a measure of glucose in the sample.

Figure 2:
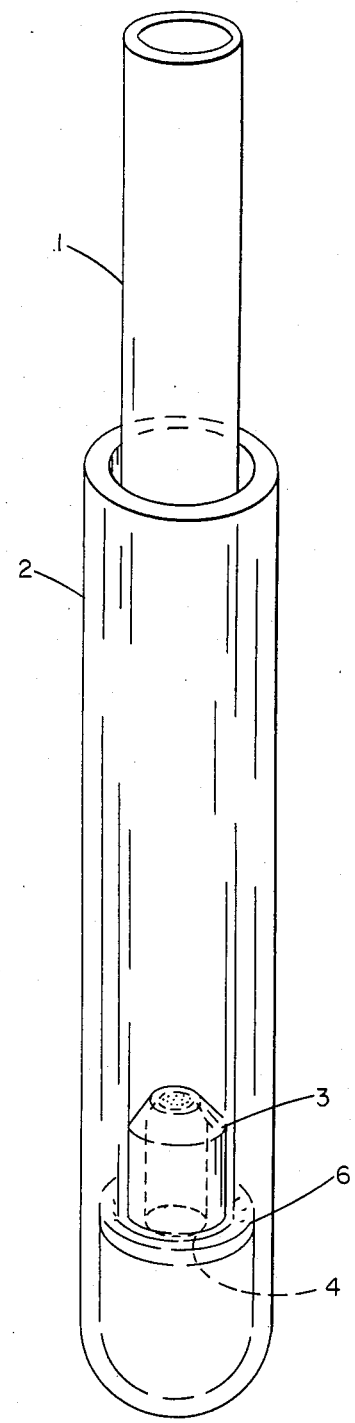
FIG. 2 is a perspective view of apparatus for carrying out one of said methods.

Apparatus useful in the practice of the peroxide assay method is illustrated in FIG. 2. The rim 6 of the plug 3 fits snugly but movably within outer tube 2. Plug 3, whose inner core contains filter 4, fits immovably in the end of inner tube 1.

The bottom of tube 2 contains an excess of a support-bound FluoraBora, described above. Into tube 1 are introduced, in aqueous solution, excesses of all of the reactants, except the compound to be assayed, necessary to produce peroxide in the procedure being measured. A sample containing an unknown amount of the compound to be assayed, e.g., glucose, is introduced into tube 1, which is then pulled up to allow the solution, including any peroxidase produced, to pass downward through filter 4 to contact the support-bound FluoraBora. After the release of fluorophore into solution has been completed, tube 1 is pushed down to allow the fluorophore in solution to pass upward through filter 4. The fluorescence of the solution, or of an extract of the solution, a measure of the compound being assayed in the sample, is measured with a fluorometer.

Other Assays

The stable bond formed between FluoraBoras and supports containing hydroxyl groups and between FluoraBoras and certain other compounds, e.g., mucopolysaccharides, provides the basis for an assay for compounds having an affinity for boronic acids. The desired FluoraBora is contacted with an unknown amount of a compound to be assayed having an affinity for boronic acids. Another material having an affinity for boronic acids, e.g., one of the supports discussed above, is then added to the mixture. This second material binds with FluoraBora which did not complex with the compound being assayed. The amount of FluoraBora bound to this second material is inversely proportional to the amount of unknown present.

Other Embodiments

Other embodiments are within the following claims. For example, many more compounds than are listed in the Tables are within the scope of the invention. Also, the assays can be varied in many conventional ways without departing from the inventive concept. For example, FluoraBoras can be used in standard displacement assays to measure compounds having an affinity for boronic acids.

TABLE I

ReportaBoras

| Structure | Trivial or Chemical Name | Utility of Reporter Group | Starting Materials |
|---|---|---|---|
| 1 | FBI | fluorescent | Dansyl chloride, m-aminophenyl boronic acid |
| 2 | FBII | fluorescent | Fluorescein isothiocyanate, m-aminophenyl boronic acid |
| 3 | FBIII | fluorescent | 4-Bromomethyl-7-methoxycoumarin, 4-carboxyphenyl boronic acid |
| 4 | FBIV | fluorescent | 4-Chloro-7-nitrobenzo-2-oxa-1,3-diazole, m-aminophenyl boronic acid |
| 5 | FBV | fluorescent | 4-Bromomethyl-7-methoxycoumarin, n-(succinamido)-3-aminophenyl boronic acid |

TABLE I-continued

ReportaBoras

| | Structure | Trivial or Chemical Name | Utility of Reporter Group | Starting Materials |
|---|---|---|---|---|
| 6 | [structure] | FBVI | fluorescent | O—phthalaldehyde, thiol, m-aminophenyl boronic acid |
| 7 | [structure] | FPBA | fluorescent | A—DARPSYL chloride, m-aminophenyl boronic acid |
| 8 | [structure] | 3-[Ferrocene carboxamido] phenyl boronic acid | electron-dense metal | Ferrocene carbonyl chloride, m-aminophenyl boronic acid |
| 9 | [structure] | CBI | colored (brownish red), | Dimethylaminonaphthoazomethoxy-phenylsulfonic acid, m-aminophenyl boronic acid |
| 10 | [structure] | CBIII | colored (reddish) | |

TABLE I-continued

ReportaBoras

| Structure | Trivial or Chemical Name | Utility of Reporter Group | Starting Materials |
|---|---|---|---|
| 11 (ferrocene-CH₂-N(SO₂-naphthyl-N(CH₃)₂)-phenyl-B(OH)₂) | Metallo FluoraBora I (MFI) | electron-dense, fluorescent | Ferrocene carboxyaldehyde, m-aminophenyl boronic acid, dansyl chloride |
| 12 ((CH₃)₂N-phenyl-N=N-phenyl-NH-C(S)-NH-phenyl-B(OH)₂) | CBII | colored (brown) | Dimethylaminophenylazophenylisothiocyanate, m-aminophenyl boronic acid |
| 13 (iminostilbene-C(O)-NH-phenyl-B(OH)₂) | carbamazepino phenylboronic acid | therapeutic | iminostilbene, phosghene, M—aminophenyl boronic acid, |
| 14 (phenyl-Hg-S-(CH₂)₃-C(O)-NH-phenyl-B(OH)₂) | MetalloBora I (MBI) | electron-dense metal | phenylmercurychloride, 1-thiopropionic acid, m-aminophenyl boronic acid |

TABLE II

CarrierCeptors

| | Structure | Trivial or chemicl name | Relative strength of adduct with boronic acids | pKa |
|---|---|---|---|---|
| 1 | morpholine-NH⁺-CH₂-CH(OH)-CH₂-SO₃⁻ | MOPSO | Weak | 6.75 |
| 2 | ⁺HN=C(CH₂OH)₃ attached to -CH₂-CH(OH)-CH₂-SO₃⁻ | TAPSO | Strong | 7.39 |

TABLE II-continued

| | Structure | CarrierCeptors Trivial or chemicl name | Relative strength of adduct with boronic acids | pKa |
|---|---|---|---|---|
| 3 | $^+HN(H)$–$CH_2$–$CH_2$–$CH_2$–$SO_3^-$, with C bearing $CH_2OH$, $CH_2OH$, $CH_2OH$ | TAPS | Fairly Strong | 8.11 |
| 4 | $^+HN(H)$–$CH_2$–$CH_2$–$SO_3^-$, with C bearing $CH_2OH$, $CH_2OH$, $CH_2OH$ | TES | Fairly Strong | 7.16 |
| 5 | $^+H$–$N(CH_2CH_2OH)(CH_2CH_2OH)$–$CH_2$–$CH_2$–$CH_2$–$SO_3^-$ | BES | moderate | 6.88 |
| 6 | $^+H$–$N(CH_2CH_2OH)(CH_2CH_2OH)$–$CH_2$–$COO^-$ | Bicine | moderate | 8.04 |
| 7 | H–$^+N(H)$–$CH_2$–$COO^-$, with C bearing $CH_2OH$, $CH_2OH$, $CH_2OH$ | Tricine | moderate | |
| 8 | $OH$–$CH_2$–$C(H)(^+NH_3)$–$COO^-$ | Serine | Weak | |
| 9 | $CH_3$–$CH(OH)$–$CH(^+NH_3)$–$COO^-$ | Threonine | Weak | |
| 10 | $NH_3^\oplus$–$CH(H)$–$NH$–$(CH_2)_3$–$N(CH_2CH_2OH)(CH_2CH_2OH)$   $Cl^-$ | | Moderate | |
| 11 | $(CH_3)_3N^+$–$(CH_2)_3$–$N(CH_2CH_2OH)(CH_2CH_2OH)$   $I^-$ | trimethyl ammonium propyl diethanolamine | Moderate | |

4,659,817

TABLE III
Formula (I) Compounds

| Structure | | Reporter Group or ReportaBora | Utility of Reporter Group | Trivial Name of Carrier-Ceptor |
|---|---|---|---|---|
| (structure 1) | 1 | FBPA | fluorescent | TAPS |
| (structure 2) | 2 | carbamazepino | therapeutic | TAPSO |
| (structure 3) | 3 | chromophore | colored | TAPSO |
| (structure 4) | 4 | diphenyl hydantoin derivative | therapeutic agent | TAPSO |
| (structure 5) | 5 | FBPA | fluorescent | TAPSO |

TABLE III-continued

Formula (1) Compounds

| Structure | | Reporter Group or ReportaBora | Utility of Reporter Group | Trivial Name of Carrier-Ceptor |
|---|---|---|---|---|
| [structure] | 6 | dansyl | fluorescent | TAPSO |
| [structure] | 7 | FBPA | fluorescent | guanidino-propyl di-ethanol-amine |
| [structure] | 8 | FBIII | fluorescent | MOPSO |
| [structure] | 9 | | | |

TABLE IV

Formula (2) Compounds

| Structure | | Name of Reporter Group | Utility of Reporter Group |
|---|---|---|---|
| [structure] | 1 | dansyl | fluorescent |

TABLE IV-continued

Formula (2) Compounds

| Structure | | Name of Reporter Group | Utility of Reporter Group |
|---|---|---|---|
| [structure] | 2 | DARPSYL | fluorescent |
| [structure] | 3 | | fluorescent |
| [structure] | 4 | phenyl mercury | electron-dense metal |

TABLE IV-continued

Formula (2) Compounds

| Structure | Name of Reporter Group | Utility of Reporter Group |
|---|---|---|
| (structure shown) | 5 | therapeutic |

*made from salicyclidene, 2-Aminonaphthalene (Frinton Laboratories); NaBH$_4$ reduction

TABLE V.

Extraction of Formula (1) Compounds by Ethyl Acetate

| | | Ethyl acetate; buffer partition |
|---|---|---|
| FBPA complexed with | MOPSO | 87 / 13 |
| | BICINE | 93 / 7 |
| | BES | 72 / 28 |
| | TAPS | 90 / 10 |
| | TES | 92 / 8 |
| | TAPSO | 67 / 33 |
| FBI complexed with | MOPSO | 92 / 8 |
| | BICINE | 71 / 29 |
| | BES | 81 / 19 |
| | TES | 93 / 7 |
| | TAPS | 84 / 16 |
| | TAPSO | 28 / 72 |
| FBIII complexed with | MOPSO | 99 / 1 |
| | BICINE | 98 / 2 |
| | BES | 95 / 5 |
| | TES | 95 / 5 |
| | TAPS | 99 / 1 |
| | TAPSO | 55 / 45 |

TABLE VI

Fluorescence of FluoraBoras in TAPSO vs ethyl acetate

| | TAPSO pH 7.4 | ETHYL ACETATE |
|---|---|---|
| FBPA | 1015 μA/μmole (370/953) | 2363 μA/μmole (370/428) |
| FBI | 8.8 μA/μmole (340/560) | 61.3 μA/μmole (340/510) |
| FBIII | 436 μA/μmole (330/410) | Quenched |

TABLE VII

Enhancement or inhibition of formula (1) compounds in serum albumin

| | | Fluorescence enhancement |
|---|---|---|
| FBPA complexed with | MOPSO | 2.8 |
| | BICINE | 2.4 |
| | BES | 1.9 |
| | TAPS | 1.7 |
| | TES | 1.5 |
| | TAPSO | 1.6 |
| FBI complexed with | MOPSO | 6.8 |
| | BICINE | 5.6 |
| | BES | 5.0 |
| | TES | 3.8 |
| | TAPS | 3.2 |
| | TAPSO | 2.4 |
| FBIII complexed with | MOPSO | 0.33 |
| | BICINE | 0.39 |
| | BES | 0.40 |
| | TES | 0.63 |
| | TAPS | 0.68 |

TABLE VII-continued
Enhancement or inhibition
of formula (1) compounds in serum albumin
| | Fluorescence enhancement |
|---|---|
| TAPSO | 0.75 |
What is claimed is:
1. A compound of the formula
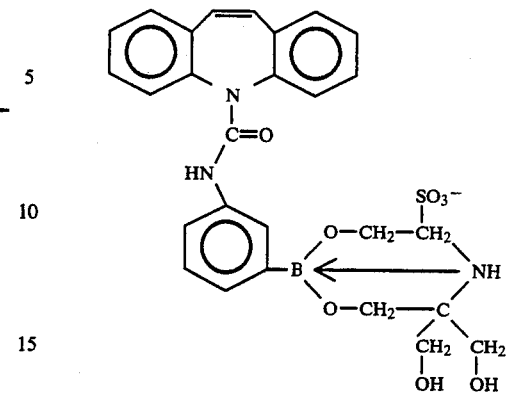
2. A compound of the formula
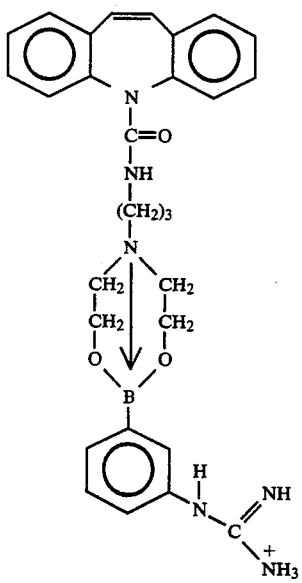
* * * * *